US012636272B2

(12) United States Patent
Wu et al.

(10) Patent No.: US 12,636,272 B2

(45) Date of Patent: May 26, 2026

(54) METHOD AND COMPOSITION FOR INHIBITING VIRUS INFECTION

(71) Applicant: ARJIL BIOTECH HOLDING COMPANY LIMITED, Hsinchu City (TW)

(72) Inventors: Yeh B. Wu, Hsinchu City (TW); Jir-Mehng Lo, Hsinchu City (TW); Hui Ju Liang, Taipei City (TW); Cheng Huang, Taipei City (TW)

(73) Assignee: ARJIL BIOTECH HOLDING COMPANY LIMITED, Hsinchu City (TW)

( * ) Notice: Subject to any disclaimer, the term of this patent is extended or adjusted under 35 U.S.C. 154(b) by 596 days.

(21) Appl. No.: 18/017,113

(22) PCT Filed: Jul. 23, 2021

(86) PCT No.: PCT/US2021/042895

§ 371 (c)(1),
(2) Date: Jan. 20, 2023

(87) PCT Pub. No.: WO2022/020676

PCT Pub. Date: Jan. 27, 2022

(65) Prior Publication Data

US 2023/0310369 A1 Oct. 5, 2023

Related U.S. Application Data

(60) Provisional application No. 63/055,619, filed on Jul. 23, 2020.

(51) Int. Cl.

*A61K 31/365* (2006.01)
*A61K 31/664* (2006.01)
*A61P 31/14* (2006.01)
*A61P 31/20* (2006.01)

(52) U.S. Cl.

CPC .......... *A61K 31/365* (2013.01); *A61K 31/664* (2013.01); *A61P 31/14* (2018.01); *A61P 31/20* (2018.01)

(58) Field of Classification Search

CPC ......... A61P 31/20; A61P 31/14; A61K 31/365
See application file for complete search history.

(56) References Cited

U.S. PATENT DOCUMENTS 9,345,687 B2 5/2016 Eriksson et al.
2018/0195063 A1 7/2018 Goldeck et al.
2022/0296565 A1* 9/2022 Rajendran ............ A61K 31/365

FOREIGN PATENT DOCUMENTS

WO WO 2016/169573 A1 10/2016

OTHER PUBLICATIONS

Boncristiani HF, Criado MF, Arruda E. Respiratory Viruses. Encyclopedia of Microbiology. 2009:500-18. doi: 10.1016/B978-012373944-5.00314-X. Epub Feb. 17, 2009. PMCID: PMC7149556) (Year: 2009).*

Lacombe, Karine, and Juergen Rockstroh. "HIV and viral hepatitis coinfections: advances and challenges." Gut 61, No. Suppl 1 (2012): i47-i58) (Year: 2012).*

Woolhouse, M., Scott, F., Hudson, Z., Howey, R. and Chase-Topping, M., 2012. Human viruses: discovery and emergence. Philosophical Transactions of the Royal Society B: Biological Sciences, 367(1604), pp. 2864-2871 (Year: 2012).*

Bomfim-Hyppólito, S., Eleuterio Jr, J., Nunes, G.C., Bomfim-Hyppólito, E., Franco, E.S. and Neto, R.D.J.P., 2013. HIV or human papillomavirus co-infection among Brazilian individuals infected with hepatitis B and/or hepatitis C. International Journal of Gynecology & Obstetrics, 122(3), pp. 258-260. (Year: 2013).*

Koumbi, L., 2015. Current and future antiviral drug therapies of hepatitis B chronic infection. World journal of hepatology, 7(8), p. 1030. (Year: 2015).*

Liu, J., Liu, W., Liu, Y., Zhou, X., Zhang, Z. and Sun, Z., 2016. Prevalence of microorganisms co-infections in human papillomaviruses infected women in Northern China. Archives of Gynecology and Obstetrics, 293(3), pp. 595-602 (Year: 2016).*

Torresi J, McGuinness S, Leder K, O'Brien D, Ruff T, Starr M, Gibney K. Non-vaccine-Preventable Infections. Manual of Travel Medicine. Oct. 19, 2019:225-64. doi: 10.1007/978-981-13-7252-0_5. PMCID: PMC7120392. (Year: 2019).*

Jones, Jennifer E., Valerie Le Sage, and Seema S. Lakdawala. "Viral and host heterogeneity and their effects on the viral life cycle." Nature Reviews Microbiology 19, No. 4 (2021): 272-282) (Year: 2021).*

Grant LM, Purres M. Viral Hepatitis. [Updated Mar. 10, 2024]. In: StatPearls [Internet]. Treasure Island (FL): StatPearls Publishing; Jan. 2025. Available from: https://www.ncbi.nlm.nih.gov/books/NBK554549/ (Year: 2025).*

Alam et al., "HIV-inhibitory diterpenoid from Anisomeles indica", Fitoterapia, 2000, vol. 71, pp. 574-576.

(Continued)

*Primary Examiner* — James H Alstrum-Acevedo
*Assistant Examiner* — Carolyn L. Ladd
(74) *Attorney, Agent, or Firm* — Birch, Stewart, Kolasch & Birch, LLP

(57) ABSTRACT

The present invention pertains to a compound, particularly ovatodiolide, for use in preventing or treating an infection of a virus, including a hepatitis virus, an influenza virus, a herpes simplex virus, an enterovirus, a rotavirus, a dengue virus, a poxvirus, a human immunodeficiency virus, an adenovirus, a coronavirus, an arenavirus, a measles virus, a retrovirus and a norovirus, particularly SARS-COV-2. Also provided are the method for preventing or treating a virus infection using the compound, and the pharmaceutical composition or composition comprising the compound.

1 Claim, 6 Drawing Sheets

(56) References Cited

OTHER PUBLICATIONS

International Search Report, issued in PCT/US2021/042895, mailed Mar. 18, 2022.
Written Opinion of the International Searching Authority, issued in PCT/US2021/042895, mailed Mar. 18, 2022.

* cited by examiner

METHOD AND COMPOSITION FOR INHIBITING VIRUS INFECTION

CROSS REFERENCE TO RELATED APPLICATIONS

This application is the National Phase of PCT International Application No. PCT/US2021/042895, filed on Jul. 23, 2021, which claims priority under 35 U.S.C. 119 (e) to U.S. Provisional Application No. 63/055,619, filed on Jul. 23, 2020, all of which are hereby expressly incorporated by reference into the present application.

FIELD OF THE INVENTION

The present invention provides a method and composition of inhibiting virus infections with a compound.

BACKGROUND OF THE INVENTION

Viruses, made of genetic material inside of a protein coating, invade living, normal cells and use those cells to multiply and produce other viruses like themselves, that may cause familiar infectious disease such as flu and warts, or may cause severe illness such as smallpox and acquired immune deficiency syndrome (AIDS).

For example, there are 5 different types of hepatitis viruses i.e., A, B, C, D and E along with X and G. Hepatitis A and E viruses are induced by consumption of pestiferous water and food. However, hepatitis B, C, and D viruses are caused by parenteral, adjoin with infected bodily fluids. In addition, hepatitis C and D virus infections are also on the increase and effective treatments are needed.

Hepatitis B virus (HBV) causes acute and chronic viral hepatitis in humans. HBV infection is often associated with severe liver diseases, including cirrhosis and hepatocellular carcinoma (HCC) [1]. The prevalence of HBV infection in the world is very high. About 350 million individuals are chronically infected, despite the availability of an effective vaccine for more than 25 years. Approximately an 100-fold increase in the relative risk of HCC among HBV carriers compared to non-carriers [2].

An increasing number of patients with HBV infection cannot use the currently approved anti-HBV drugs, including interferon alpha or nucleos(t)ide analogues that inhibit the viral reverse transcriptase, due to the adverse effects and the emergence of drug resistance [3].

Therefore, the search for effective and safe as well as affordable anti-HBV agents aiming at the interference with other steps in the viral life cycle is required to improve the treatment outcome.

HBV is a small DNA virus consisting of a nucleocapsid which protects the 3.2 kb viral genome [4]. The HBV nucleocapsid is surrounded by an envelope, consists of hepatitis B surface antigens (HBsAgs). HBsAgs are encoded in one open reading frame with three in-phase start codons. The MHBsAg has a 55-amino-acid (aa) extension from the S domain that is known as the pre-S2 domain. The LHBsAg has a further 108-aa region that extends from the pre-S2 domain to compose the pre-S1 domain. Recently, sodium taurocholate cotransporting polypeptide (NTCP) was identified as an HBV receptor [5, 6]. Entry of HBV into uninfected hepatocytes has long been proposed as a potential target for antiviral intervention [7]. On the other hand, HepG2.2.15 cells encompass HBV whole genome, which was widely used to study HBV replication, assembly, and secretion.

The attachment to hepatocyte by HBV during infection has long been proposed to be a potential target for antiviral intervention. It is thought that molecules specifically binding to HBV particles may interfere with viral attachment and hence reduce or block subsequent infection [8].

Insights into the early infection events of human HBV are limited because of the lack of a cell culture system supporting the full replication cycle. To date, two cell types have been shown to be susceptible to HBV infection. One is the human hepatoma cell line HepaRG, which becomes infectable after dimethyl sulfoxide (DMSO)-induced differentiation [7,9], while the other cell type, normal human primary hepatocytes, is readily infected by HBV [10, 11], but the limited lifetime of the cells in vitro and the lack of a consistent source severely restrict its further application.

Besides, Herpes simplex virus (HSV) also consists of a DNA genome encased within a protein coating. Herpes simplex virus types 1 and 2 (HSV-1 and HSV-2) are the causative agents of human diseases, including gingivostomatitis, pharyngitis, herpes labialis, encephalitis, eye and genital infection [12]. Herpesvirus infections generally involve a mild or asymptomatic primary phase followed by persistence of the virus in a non-replicating latent state or at a clinically undetectable level of replication [13]. Primary infection with HSV-1 most commonly involves the mouth and/or throat resulting in gingivostomatitis and pharyngitis. Following recovery from the primary oropharyngeal infection, the individual retains HSV DNA in the trigeminal ganglion for life and may suffer recurrent attacks of herpes labialis. Studies have also revealed a possible association between some members of the herpesvirus family and periodontal diseases [14]. Human herpesviruses may occur in periodontitis lesions with relatively high prevalence [15]. HSV is related to the severity of periodontal diseases in terms of clinical attachment loss [16]. Viral gingival infections may act to impair host defense mechanisms and thereby set the stage for overgrowth of pathogenic oral bacteria [15, 17].

HSV commonly attacks mucosa, skin, eyes and the nervous system and is capable of infecting a wide variety of cells [18]. Human gingival mucosa organ culture can be infected with HSV-1 and HSV-2 [19]. In addition, human gingival keratinocytes and gingival fibroblasts which are grown in vitro support the multiplication of HSV [20, 21]. HSV-1 encodes viral thymidine kinase, which indirectly metabolizes acyclovir into acyclovir triphosphate, a chain terminator substrate for HSV DNA polymerase and stops viral DNA replication [22]. However, resistance of HSV to acyclovir has been reported in 5-30% of cases [23]). Acyclovir-resistant HSV-1 strains occur frequently in immunocompromised patients, which may result in severe complications [24]. Due to the lack of vaccine, topical microbicides may be an important strategy for preventing HSV transmission.

Severe acute respiratory syndrome (SARS) outbreak in November 1st, 2002 to Jun. 18, 2003 led to 801 deaths in over 29 countries and 8465 probable cases around the world according to the World Health Organization (WHO) [25]. SARS, an enveloped β coronavirus containing positive-sense, single-stranded RNA, has a genome size of about 30 kb, in which open reading frame (ORF) 1a and 1b encode for two respective polyproteins (pps), pp1a and pp1ab [26, 27]. To complete its lifecycle, successful replication and proteolytic processing are imperative [28]. Indeed, the consensus functions of these virus-encoded proteolytic proteins are found in all coronaviruses, specifically papline-like protease (PLpro) and chymotrypsin-like protease (3CLpro) [28]. In proteolytic processing of pp1a and pp1ab, PLpro and 3CLpro cleave the first three sites and the remaining 11 locations, respectively, yielding a total of 16 nonstructural proteins (nsp1-16) [26, 27]. Thus, 3CLpro inhibition has been regarded as a molecular approach in anti-SARS drug discovery and developments [25, 29].

SARS-COV-2 is a novel coronavirus that spreads rapidly since its identification in patients with severe pneumonia in Wuhan, China (named as COVID-19), has been reported in 25 countries, with nearly 72000 laboratory-confirmed cases and a death toll of 1775 worldwide as of Feb. 17, 2020 [30]. Devastatingly, no drag or vaccine has yet been approved to treat human coronaviruses [3]. Concerning the current outbreak of SARS-CoV-2 and the therapeutic experience of SARS and MERS (another β coronavirus), many studies extensively investigate the possibility of using the existing antiviral agents used for HIV, hepatitis B virus, hepatitis C virus and influenza infections for the treatment or intervention of SARS-COV-2 [31, 32]. In the meantime, SARS-COV-2 has been characterized as an enveloped, positive-sense, single-stranded RNA β coronavirus, similar to SARS and MERS [31]. Consistent with the characteristics of coronaviruses, SARS-Cov-2 genome encodes structural proteins (e.g., spike glycoproteins), nonstructural proteins (e.g., 3CLpro, PLpro, helicase, RNA-dependent RNA polymerase), and accessory proteins. Regarding the available genomic sequence of SARS-COV-2, SARS and MERS, a high-level conservation of the proteolytic sites and proteolytic enzymes was found, whence repurposing SARS and MERS protease inhibitors for treatment of SARS-COV-2 is worth considering [33]. As 3CLpro plays a pivotal role in SARS, it is reasonable to approach protease inhibition by targeting the 3CLpro of SARS-COV-2 instead of its PLpro to intercept its lifecycle [25, 29, 33].

Currently, disulfiram, an approved drug to treat alcohol dependence, has been reported to inhibit the PLpro of MERS and SARS in cell cultures but has yet been evaluated clinically [31]. In addition, clinical trials of HIV protease inhibitors (lopinavir and ritonavir) in SARS-COV-2 patients have also commenced, yet it is uncertain if it can effectually inhibit those of SARS-COV-2, as HIV and β coronavirus proteases belong to the aspartic protease family and the cysteine protease family, respectively [31, 34]. On the other hand, remdesivir (RDV), a nucleotide analog of RNA dependent RNA polymerase inhibitor approved for HIV treatment, is currently under clinical trials in SARS-COV-2 patients with estimated completion dates in April, 2020; galidesivir, another nucleotide analog of RNA dependent RNA polymerase inhibitor in early-stage clinical studies for HCV treatment, has shown broad-spectrum antiviral activities against severe acute respiratory syndrome (SARS), Middle East respiratory syndrome (MERS) in preclinical studies [34, 35]. However, one might expect that a nucleoside analog can elicit toxicity that are still beyond our knowledge [36].

There are yet to find antiviral drugs to prevent or treat human coronavirus infections. There is an urgent need for exploring and developing a safe anti-coronavirus therapy, particularly against SARS-COV-2.

Still, it is desirable to develop a new antiviral therapy or medicament.

BRIEF SUMMARY OF THE INVENTION

It is unexpectedly found in the present invention that some compounds are effective in inhibition of virus infections, especially a Hepatitis B virus (HBV) infection and/or a Herpes simplex virus (HSV) infection and/or a coronavirus infection.

In one aspect, the present invention provides a method for preventing or treating a virus infection, comprising administering to a subject in need thereof a compound having the structure of formula (I)

(I)

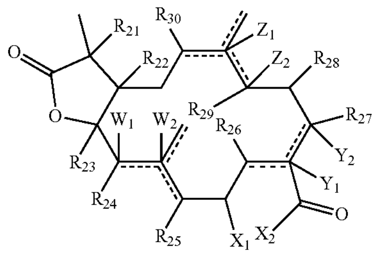

wherein each of $R_{21}$, $R_{22}$, $R_{23}$, $R_{24}$, $R_{25}$, $R_{26}$, $R_{27}$, $R_{28}$, $R_{29}$, $R_{30}$, $X_1$ and $X_2$ is H, OH, $C_{1-8}$ alkyl, NRx, SRx, ORx, pyrazoline, cysteine, glutathione, halogen, COORx, or COO$(CH_2)n$-$CH_3$; n is an integer from 0-3; each of $Y_1$, $Y_2$, $Z_1$, $Z_2$, $W_1$ and $W_2$ is H, OH, $C_{1-8}$ alkyl, or $X_1$ and $X_2$ together form —O—, or $Y_1$ and $Y_2$, $Z_1$ and $Z_2$, or $W_1$ and $W_2$ together form an epoxy.

In the examples of the invention, the compounds were confirmed to be able to inhibit a virus replication, an assembly or a release of viral particles.

In the examples of the present invention, to evaluate the effect of prospecting drugs on proteolytic processing inhibition in high-throughput, the synthetic peptides labelled fluorescence resonance energy transfer (FRET) pairs were employed as those used in the previous studies, in which the quenched fluorophore is released upon cleavage of the FRET-labelled peptides, generating fluorescent signals that can be monitored in real-time [25, 29, 37]. It is confirmed in the present invention that any or its mixture of the compounds disclosed herein is effective in inhibition of a cysteine protease, particularly 3CLpro of SARS-COV-2.

According to the invention, the virus is selected from the group consisting of a hepatitis virus, an influenza virus, a herpes simplex virus, an enterovirus, a rotavirus, a dengue virus, a poxvirus, a human immunodeficiency virus, an adenovirus, a coronavirus, an arenavirus, a measles virus, a retrovirus and a norovirus.

In one example, the present invention to provide a method for preventing or treating an HBV infection, comprising administering to a subject in need thereof the compound of formula (I).

In another example, the present invention to provide a method for preventing or treating an HSV infection, comprising administering to a subject in need thereof the compound of formula (I).

In another example, the present invention to provide a method for preventing or treating a coronavirus infection, comprising administering to a subject in need thereof the compound of formula (I).

Actually, it would be derived from the findings that the inhibition of hepatitis virus infection by inhibiting the virus replication, the assembly, the release of viral particles, and the entry of virus to develop a broad-spectrum antiviral agent because the compound inhibited the development of viruses.

In another aspect, the present invention provides a composition/pharmaceutical composition for preventing or treating a virus infection, which comprises a therapeutically effective amount of the compound of formula (I), and a pharmaceutically acceptable carrier.

In one further aspect, the present invention provides a use of the compound of formula (I) for manufacturing a medicament for treating or preventing a virus infection.

In one further aspect, the present invention provides a composition/pharmaceutical composition for preventing or treating an infection of a coronavirus, particularly SARS-COV-2, comprising a therapeutically effective amount of any of the compounds disclosed herein or pharmaceutically acceptable salts thereof, or its mixture, in combination of a pharmaceutically acceptable carrier.

Optionally, the composition/pharmaceutical composition according to the invention may comprise at least one additional anti-viral therapeutic agent.

In one yet aspect, the present invention provides a use of any of the compounds disclosed herein or pharmaceutically acceptable salts thereof, or its mixture for manufacturing a medicament for preventing or treating an infection of a coronavirus, particularly SARS-COV-2.

In some examples of the invention, the compound may be one or more selected from the group consisting of:

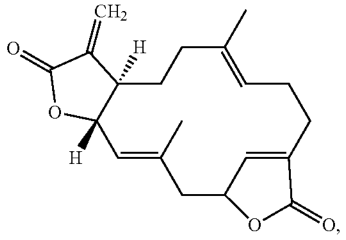

(ovatodiolide)

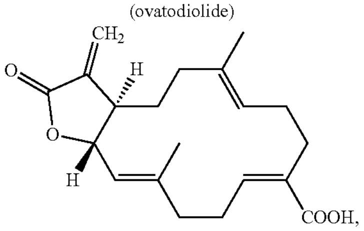

(ovatodiolide acid)

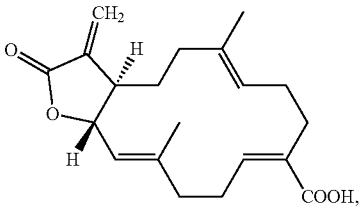

(anisomelic acid)

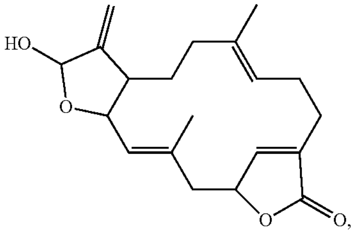

-continued

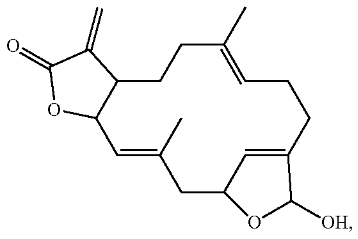

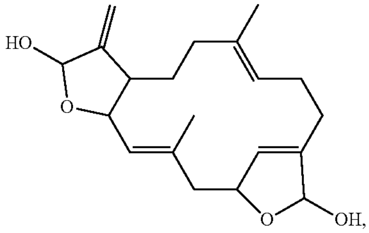

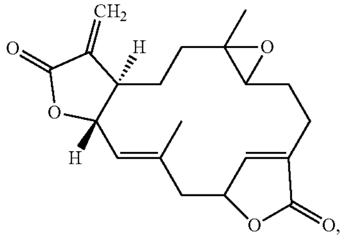

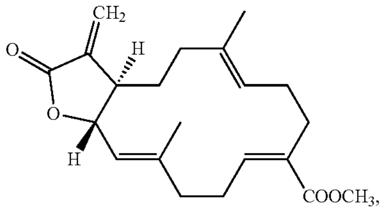

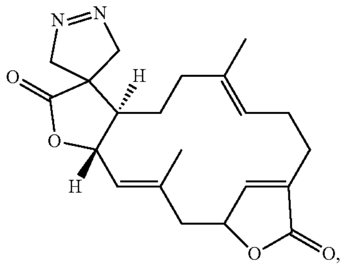

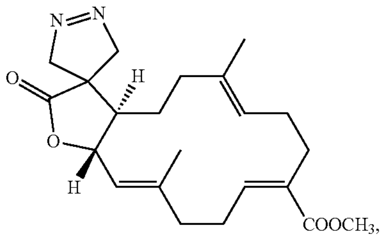

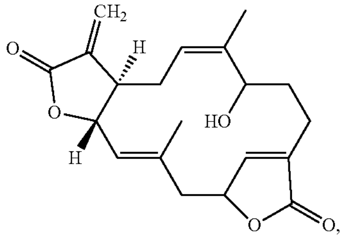

-continued

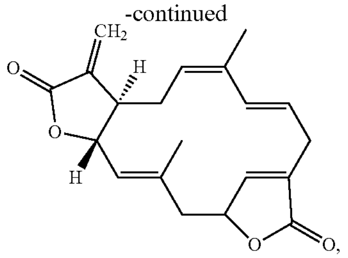

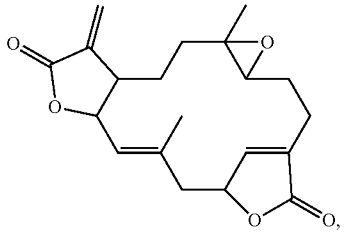

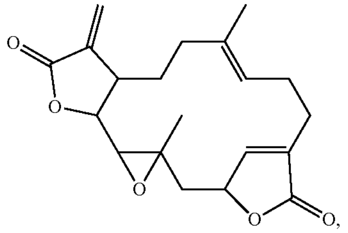

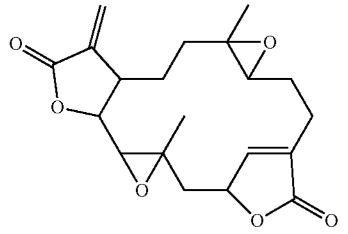

and its derivatives.

In one particular example of the invention, the compound of formula (I) is

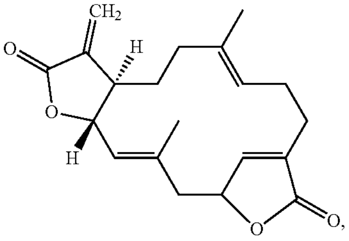

(ovatodiolide)

called as AR100-DS1 herein.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1A:
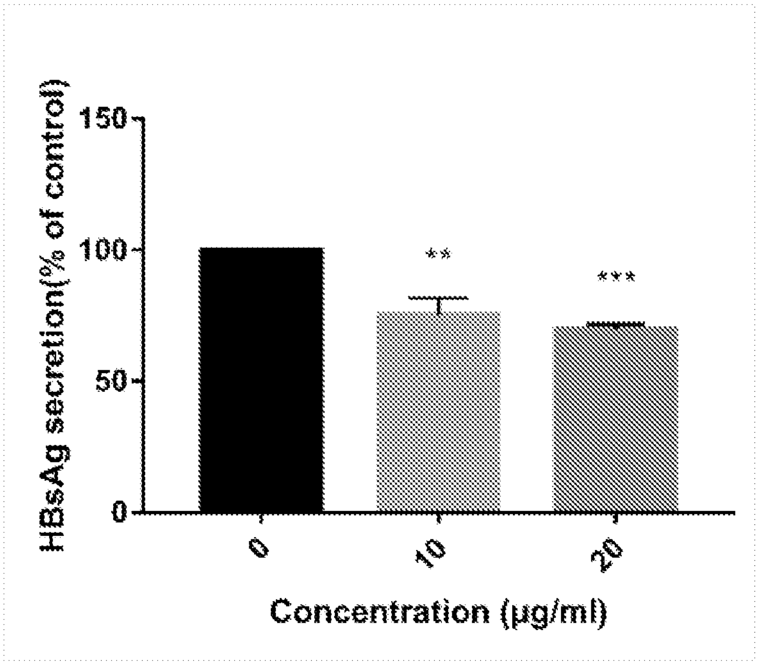
FIG. 1A shows the effects of AR100-DS1 at 0, 10 and 20 μg/ml on HBsAg secretion of HepG2.2.15 cells (*, P<0.05; , P<0.01; *, P<0.001).
Figure 1B:
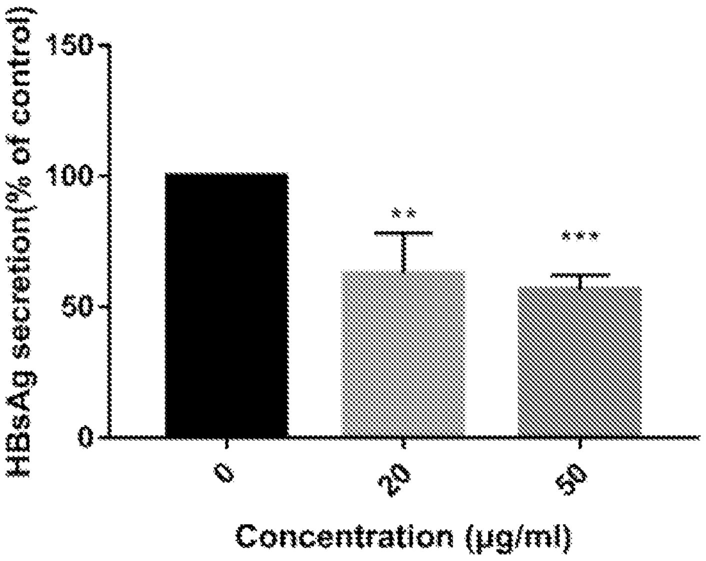
FIG. 1B shows the effects of AR100-DS1 at 0, 20 and 50 μg/ml on HBsAg secretion of HepG2.2.15 cells (*, P<0.05; , P<0.01; *, P<0.001).
Figure 1C:
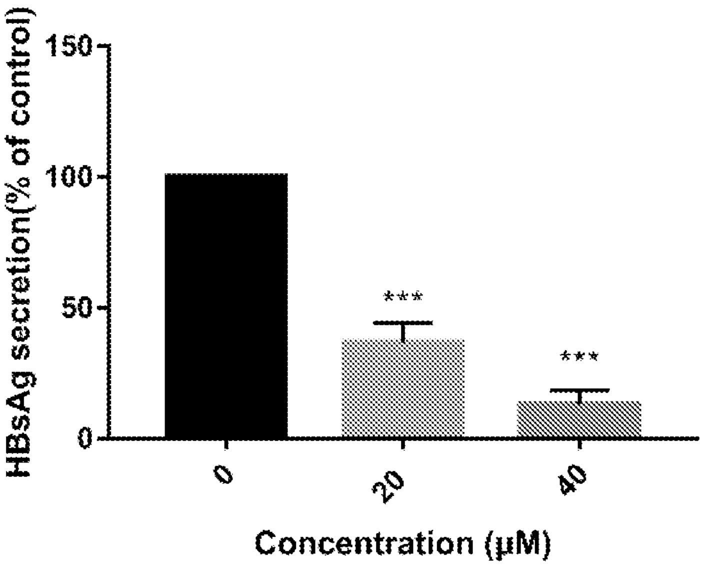
FIG. 1C shows the effects of AR100-DS1 at 0, 20 and 40 μg/ml on HBsAg secretion of HepG2.2.15 cells (*, P<0.05; , P<0.01; *, P<0.001).

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Unless defined otherwise, all technical and scientific terms used herein have the same meaning as commonly understood by a person skilled in the art to which this invention belongs.

As used herein, the singular forms “a”, “an”, and “the” include plural referents unless the context clearly dictates otherwise. Thus, for example, reference to “a sample” includes a plurality of such samples and equivalents thereof known to those skilled in the art.

The present invention provides a method for preventing and/or treating a virus infection, comprising administering to a subject in need thereof a compound having the structure of formula (I)

(I)

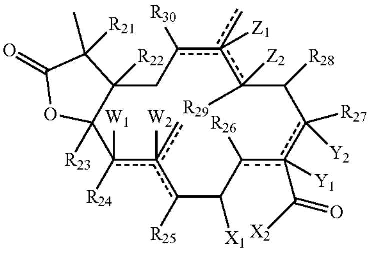

wherein each of $R_{21}$, $R_{22}$, $R_{23}$, $R_{24}$, $R_{25}$, $R_{26}$, $R_{27}$, $R_{28}$, $R_{29}$, $R_{30}$, $X_1$ and $X_2$ is H, OH, $C_{1-8}$ alkyl, NRx, SRx, ORx, pyrazoline, cysteine, glutathione, halogen, COORx, or COO $(CH_2)n-CH_3$; n is an integer from 0-3; each of $Y_1$, $Y_2$, $Z_1$, $Z_2$, $W_1$ and $W_2$ is H, OH, $C_{1-8}$ alkyl, or $X_1$ and $X_2$ together form —O—, or $Y_1$ and $Y_2$, $Z_1$ and $Z_2$, or $W_1$ and $W_2$ together form an epoxy.

The present invention provides a method for inhibiting a virus infection, wherein the compound is a compound of formula (I).

The present invention provides a composition/pharmaceutical composition for preventing and/or treating a virus infection, which comprises a therapeutically effective amount of a compound of formula (I), and a pharmaceutically acceptable carrier.

The present invention also provides a use of the compound of formula (I) for manufacturing a medicament for treating or preventing a virus infection.

The term "virus" as used herein refers to any virus, which is a small infectious agent that replicates only inside the living cells of an organism, which can infect all types of life forms, from animals and plants to microorganisms, including bacterials and *archaea*. Exemplified viruses include, without limitation, a hepatitis virus, an influenza virus, a herpes simplex virus (HSV), an enterovirus, a rotavirus, a dengue virus, a poxvirus, a human immunodeficiency virus, an adenovirus, a measles virus, a retrovirus, a coronavirus or a norovirus.

The term "Hepatitis virus" as used herein refers to a virus causing hepatitis, particular a Hepatitis B virus (HBV), Hepatitis C virus (HCV), Hepatitis D virus (HDV).

The term "coronavirus" as used herein refers to a Coronaviruse in the subfamily Orthocoronavirinae, the family Coronaviridae, order Nidovirales, and realm Riboviria, which is enveloped viruses with a positive-sense single-stranded RNA genome and a nucleocapside of helical symmetry. They have characteristic club-shaped spikes that project from their surface, which in electron micrographs create an image reminiscent of the solar corona from which their name derives. Coronaviruses cause diseases in mammals and birds, including humans. In humans, coronaviruses cause respiratory tract infections, including common cold, severe acute respiratory syndrome (SARS), Middle East respiratory syndrome (MERS), and SARS-COV-2.

The term "cysteine protease" as used herein refers to thiol proteases, are enzymes that degrade proteins, sharing a common catalytic mechanism that involves a nucleophilic cysteine thiol in a catalytic triad or duad. One example of cysteine protease in a virus is 3CLpro in SARS-COV-2.

The term "preventing" or "prevention" as used herein refers to as used herein refers to the application or administration of a composition including one or more active agents to a subject before the subject afflicted with a disease, a symptom or conditions of the disease, with the purpose to prevent from the disease, the symptoms or conditions of the disease, or inhibit the progression of the disease.

The term "treating" or "treatment" as used herein refers to the application or administration of a composition including one or more active agents to a subject afflicted with a disease, a symptom or conditions of the disease, or a progression of the disease, with the purpose to cure, heal, alleviate, relieve, alter, remedy, ameliorate, improve, or affect the disease, the symptoms or conditions of the disease, the disabilities induced by the disease, or the progression of the disease.

The term "subject" as used herein includes human or non-human animals, such as companion animals (e.g. dogs, cats, etc.), farm animals (e.g. cattle, sheep, pigs, horses, etc.), or experimental animals (e.g. rats, mice, guinea pigs, etc.).

The term "therapeutically effective amount" as used herein refers to an amount of a pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, the therapeutically effective amount of the compound is formulated as a pharmaceutical composition for administration. Accordingly, the invention further provides a pharmaceutical composition comprising a therapeutically effective amount of the preparation of *Antrodia camphorata* or the active compounds isolated from *Antrodia camphorata*, and one or more pharmaceutically acceptable carriers.

For the purpose of delivery and absorption, a therapeutically effective amount of the active ingredient according to the present invention may be formulated into a pharmaceutical composition in a suitable form with a pharmaceutically acceptable carrier. Based on the routes of administration, the pharmaceutical composition of the present invention comprises preferably from 0.1% to 100% in weight of the total weight of the active ingredient.

The term "pharmaceutically acceptable carrier" used herein refers to a carrier(s), diluent(s) or excipient(s) that is acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation. According to the invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art.

Exemplified viruses which are responsive include, without limitation, a hepatitis virus, an influenza virus, a herpes simplex virus, an enterovirus, a rotavirus, a dengue virus, a poxvirus, a human immunodeficiency virusor, an adenovirus, a coronavirus infection, an arenavirus infection, a measles virus, a coronavirus or a norovirus. Preferably, the virus is a hepatitis virus, including a hepatitis B virus, a hepatitis C virus, a hepatitis D virus, a SARS, a MERS or a SARS-COV-2.

In one preferred example, the virus is a hepatitis B virus (HBV).

In one preferred example, the virus is a herpes simplex virus (HSV).

In one preferred example, the virus is a SARS-COV-2.

In one further aspect, the present invention provides a composition/pharmaceutical composition for treating or preventing a virus infection through inhibiting a cysteine protease in a virus, which comprises any of the compounds disclosed herein, pharmaceutically acceptable salt thereof, or its mixture. Optionally, the composition/pharmaceutical composition may comprise at least one additional anti-viral therapeutic agent.

In one further aspect, the present invention provides a use of any of the compounds disclosed herein for manufacturing a medicament for treating or preventing a virus infection through inhibiting a cysteine protease in a virus.

It was found in the present invention that the compound of formula (I) was effective in inhibiting a virus replication, an assembly or a release of viral particles.

According to the invention, the compound of formula (I) may be:

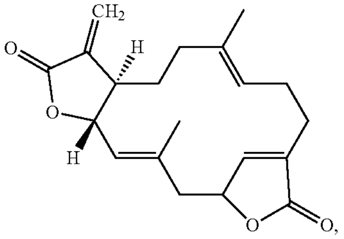

(ovatodiolide)

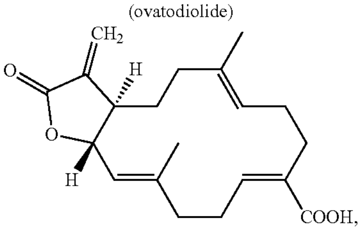

(ovatodiolide acid)

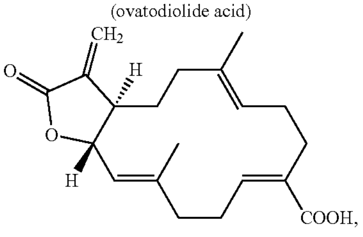

(anisomelic acid)

-continued

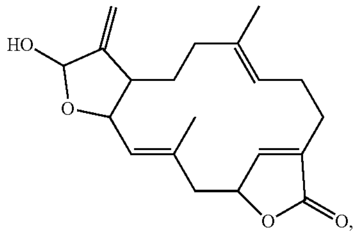

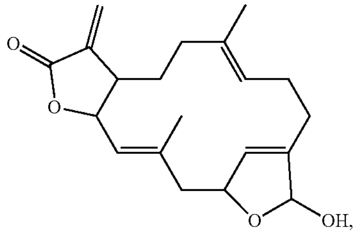

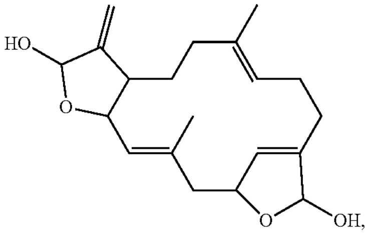

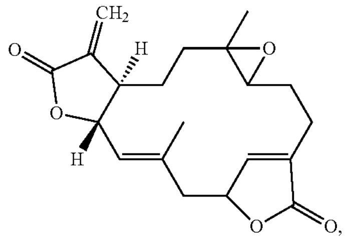

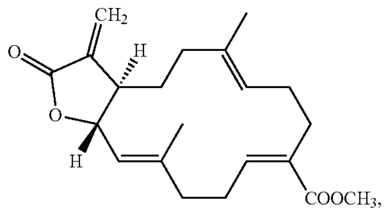

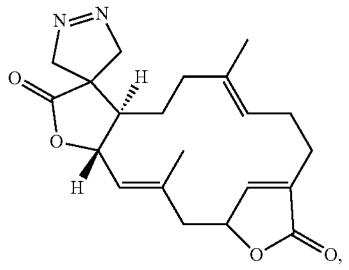

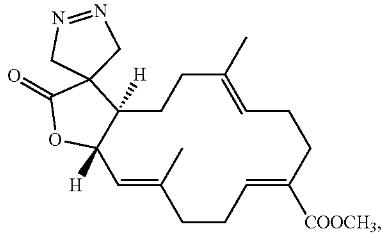

-continued

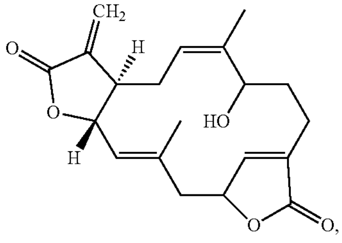

, or

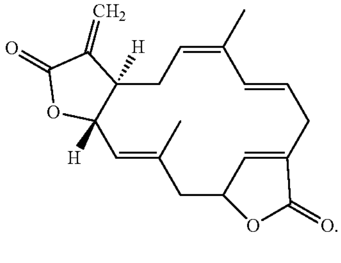

.

According to the invention, the compound of formula (I) may also be one of the derivative thereof selected from the group consisting of:

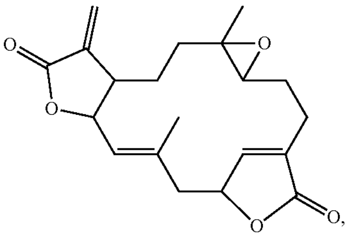

,

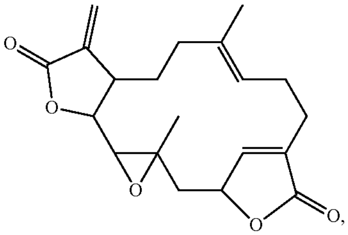

, or

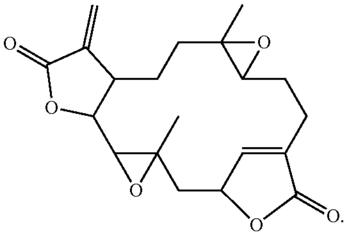

.

In one particular example of the invention, the compound of formula (I) is

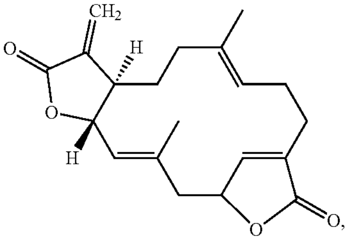

, (ovatodiolide)

called as AR100-DS1 herein.

The present invention is further illustrated by the following examples, which are provided for the purpose of demonstration rather than limitation.

EXAMPLES

1. Materials and Methods

1.1 HepG2.2.15 Cells

Continuous HBV proliferation can be achieved in HepG2.2.15 cells (RRID:CVCL_L855) stably transfected with the HBV genome of the adw2 subtype. HepG2.2.15 cells are used because of the unlimited supply and constant quality and were maintained in Dulbecco's modified Eagle medium (DMEM; Invitrogen) supplemented with 10% heat-inactivated fetal bovine serum (FBS; Thermo) plus 100 units of penicillin and 100× g of streptomycin per ml (both from Invitrogen).

1.2 HuS-E/2 Cells

HuS-E/2 cells that retains primary hepatocyte characteristics even after prolonged culture are utilized for HBV infection. For HBV infection, HuS-E/2 cells were differentiated with 2% DMSO for 7 days, and virus particles were collected to infect and replicate in HuS-E/2 cells as described in our previous study [38]. These cells are useful to assay infectivity of HBV strains, and screening of anti-HBV agents.

1.3 Collection of HBV Particles

The culture medium from drug-treated HepG2.2.15 cells is clarified by centrifugation at 1,000× g at 4° C. for 10 min, and then the supernatant is layered on top of a 20% sucrose cushion (20% sucrose, 20 mM HEPES, pH 7:4, 0.1% bovine serum albumin [BSA]) and centrifuged at 197,000× g for 3 h at 4° C. to pellet the HBV particles, which are then concentrated 100 fold to detect HBV DNA.

1.4 DNA and RNA Isolation, Reverse Transcription and Real-Time PCR

Total DNA is extracted with a Genomic DNA isolation kit (Nexttee Biotechnologie, Germany). Total RNA is isolated from cultured cells using TRIzol® reagent (Invitrogen). Reverse transcription is performed with the RNA templates, AMV reverse transcriptase (Roche), and oligo-dT primer. The products are subjected to real-time PCR with primer sets of specific genes and SYBR Green PCR Master Mix (Bio-Rad). The primer sets used for HBV core, HBsAg, cccDNA and GAPDH are described [3]. The results are analyzed with the iCycler iQ real-time PCR detection system (Bio-Rad). Plasmid p1.3HBcl is prepared at 10-fold dilutions ($2*10^4$-$2*10^9$ copies/ml) to generate a standard curve in parallel PCR reactions.

1.5 Enzyme-Linked Immunosorbent Assay (ELISA)

The HBsAg ELISA Kit (General Biologicals Corp.) are used to detect hepatitis B surface antigen (HBsAg) with the protocol suggested.

1.6 Statistical Analysis

All values are expressed as mean=SE. Each value is the mean of at least three experiments in each drug in vitro experiments. Student's t-test is used for statistical comparison. * indicates that the values are significantly different from the control (* p<0.05; , P<0.01; *, P<0.001).

1.7 FRET Protease Assays with the SARS-CoV-2 3CLpro

The establishment of an ED-FRET platform follows the protocol given by Jo et al. (2020)[29]. Briefly, a custom proteolytic, fluorogenic peptide with DABCYL and EDANS on ends, DABCYL-TSAVLQSGFRKMG-EDANS (Genomics, Taiwan), contains the consensus nsp4/nsp5 cleavage sequence that can be recognized by 3CLpro of SARS-COV-2. The peptide is dissolved in distilled water and incubated with 3CLpro of SARS-COV-2. Measurements of the spectral-based fluorescence are determined by a SPARK® multimode microplate reader provided by TECAN. The proteolytic activity is determined at 37° C. by fluorescent intensity of EDANS upon peptide hydrolysis as a function of time, in which $\lambda_{excitation}$=340 nm, $\lambda_{emission}$=490 nm, bandwidths=9, 15 nm, respectively. Prior to the assay, the emission wavelength of the testing drugs at 340 nm. excitation is examined to ensure that it does not overlap with the emission spectrum of EDANS.

Assays are conducted in triplicate in black 96-well microplates (Greiner) in 100 µL assay buffers containing 3CLpro of SARS-COV-2 and the customized peptide. In SARS 3CLpro assay, 1 µM SARS-COV-2 3CLpro containing 50 mM Tris pH 6.5 is incubated with 5 µM fluorescent substrate at 37° C. for 3 h before measuring Relative Fluorescence Unit (RFU).

1.8 Inhibition Assays in the Present of AR100-DS1

At first, the SARS-COV-2 3CLpro and the compound according to the invention, AR100-DS1, or the combination of AR100-DS1 and remdesivir (RDV), were mixed and pre-incubated at 37° C. for 1 h. Those manifesting inhibitory activity against 3CLpro of SARS-COV-2 were investigated further at different concentrations to characterize their IC50 values, using GraphPad Prism 7.03 (GraphPad Software, San Diego, CA, USA).

Based the knowledge and sequence-based SARS-COV-2 3CLpro, the efficacy of 3CLpro inhibiting AR100-DS1 were assessed in vitro to determine their therapeutic potential in SARS-COV-2 treatment. Concerning that no drug or vaccine has yet been approved to treat human SARS-COV-2 infection, developing a broad-spectrum antiviral agent to combat against SARS-COV-2 is of utmost importance and urgency. Enactment of ED-FRET technology and its workflow provided a robust, high-throughput drug discovery in the lab. Meanwhile, AR100-DS1 acts as guidelines of probable therapeutic doses in clinical assessment and prompts patent application in the future, contributing to antiviral library construction.

1.9 Plaque Reduction Assay

Plaque reduction assay was performed in triplicate in 24-well tissue culture plates. The Vero E6 cells (ATCC® CRL-1586™) were seeded at $2\times10^5$ cells/well in DMEM with 10% FCS and antibiotics one day before infection. SARS-COV-2 (NTU13, GISAID: EPI_ISL_422415)(50-100 plaque forming unit (PFU)/well) was added to the cell monolayer for 1 hour at 37° C. Subsequently, viruses were removed and the cell monolayer was washed once with PBS before covering with media containing methylcellulose and test article at the indicated concentrations for 5-7 days. The cells were fixed with formaldehyde overnight. After removal of overlay media, the cells were stained with crystal violet and the plaques were counted. The percentage of inhibition was calculated as $[1-(VD/VC)]\times100\%$, where VD and VC refer to the virus titer in the presence and absence of the test article, respectively. The half maximal effective concentration (EC50) was calculated by regression analysis of the dose-response curves generated from plaque assays.

2. Experiment Results 2.1 Effects of AR100-DS1 on the HBV Secretion in HepG2.2.15 Cells To test whether AR100-DS1 had any effect on HBV genome replication, assembly, or secretion, HepG2.2.15 cells that were stably transfected with HBV genome, were used to incubate with AR 100-DS1 for 48 hours, then HBsAg and HBV DNA collected from medium were measured by ELISA and real-time PCR. The results were shown in FIGS. 1.

The effects of AR100-DS1 on HBsAg secretion of HepG2.2.15 cells were shown in FIGS. 1A (0, 10 and 20 µg/ml of AR100-DS1) and 1B (0, 20 and 50 µg/ml of AR100-DS1) and 1C (0, 20 and 40 µg/ml of AR100-DS1). It was found that the secretion of HBsAg was inhibited and reduced to 75.25% after the treatment of 10 µg/ml of AR100-DS1, to 69.77%, 63.00% after the treatment of 20 µg/ml of AR100-DS1, and to 56.78% after the treatment of 50 µg/ml of AR100-DS1 (see FIGS. 1A and 1B). The secretion of HBsAg was significantly inhibited by the treatment of AR100-DS1 (see FIG. 1C).

Figure 1D:
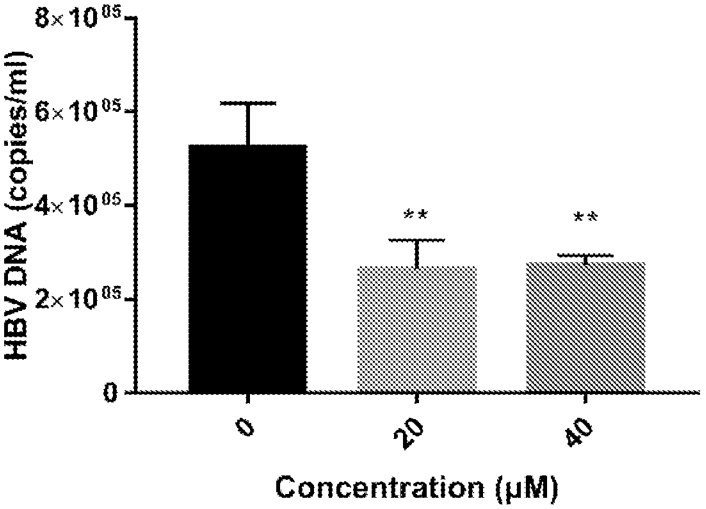
FIG. 1D shows the effects of AR100-DS1 at 0, 20 and 40 μg/ml on HBV DNA level in the culture medium of HepG2.2.15 cells (*, P<0.05; , P<0.01; *, P<0.001).

The effects of AR100-DS1 on the HBV DNA level in medium were shown in FIG. 1D (0, 20 and 40 µg/ml of AR100-DS1). It was found that the DNA level was significantly reduced after the treatment of either 20 µg/ml of AR100-DS1 or 40 µg/ml of AR100-DS1. These results showed that AR100-DS1 suppressed HBV secretion in HepG2.2.15 cells.

2.2 Effects of AR100-DS1 on HBV Infectivity and on the Viability of HuS-E/2 Cells and HepG2.2.15 Cells To evaluate the effects of AR100-DS1 on HBV infectivity and replication, HuS-E/2 cells were infected with any subtype HBV derived from HepG2.2.15 cells. The AR100-DS1 was added to the medium during infection with HBV for 18 h, then the infected cells were washed and incubated in fresh medium for 48 hours, when HBsAg in culture medium were detected by ELISA and HBV mRNA was detected by real-time PCR as an index of efficiency of HBV infection in HuS-E/2 cells. The results were shown in FIGS. 2A and 2B.

Figure 2A:
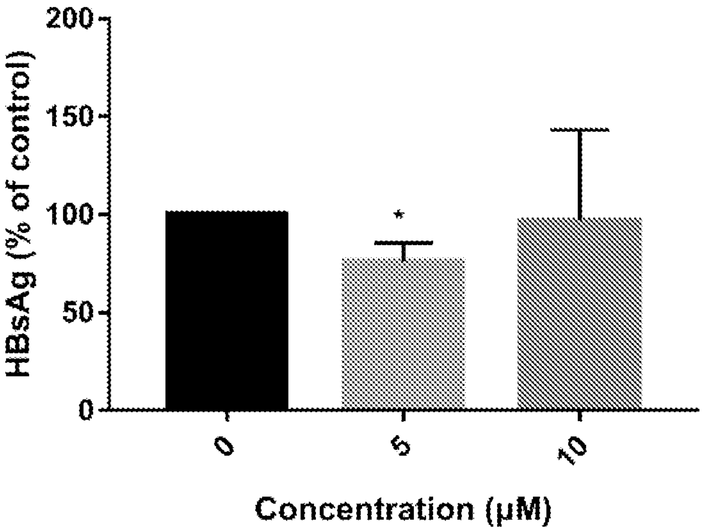
FIG. 2A shows the effects of AR100-DS1 at 0, 5 and 10 μg/ml on HBsAg secretion of HuS-E/2 cells (*, P<0.05; , P<0.01; *, P<0.001).
Figure 2B:
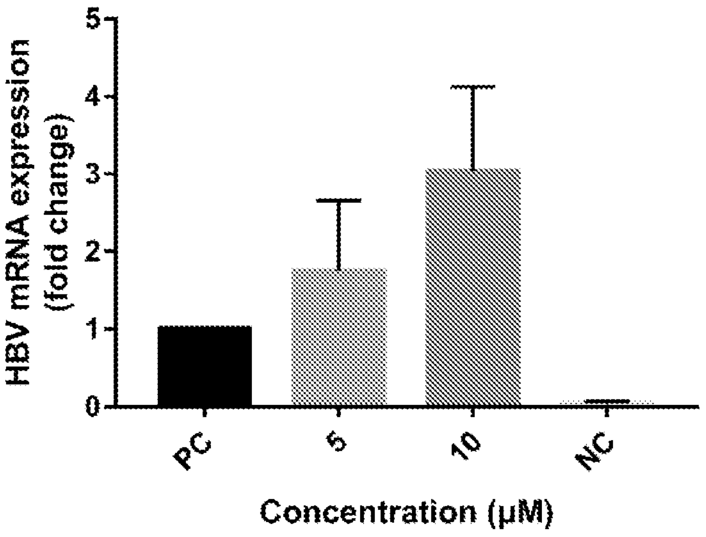
FIG. 2B shows the effects of AR100-DS1 at 0, 5 and 10 μg/ml on HBV mRNA expression level of HuS-E/2 cells.

The effects of AR100-DS1 on the entry of HBV in HuS-E/2 cells were shown in FIG. 2A (0, 5 and 10 of AR100-DS1) and 2B (0, 5 and 10 of AR100-DS1). It was found that neither secretion of HBsAg in the medium nor HBV mRNA expression level showed dose-dependent reduction. Therefore, AR100-DS1 could not prevent HBV entering into HuS-E/2 cells.

Figure 2C:
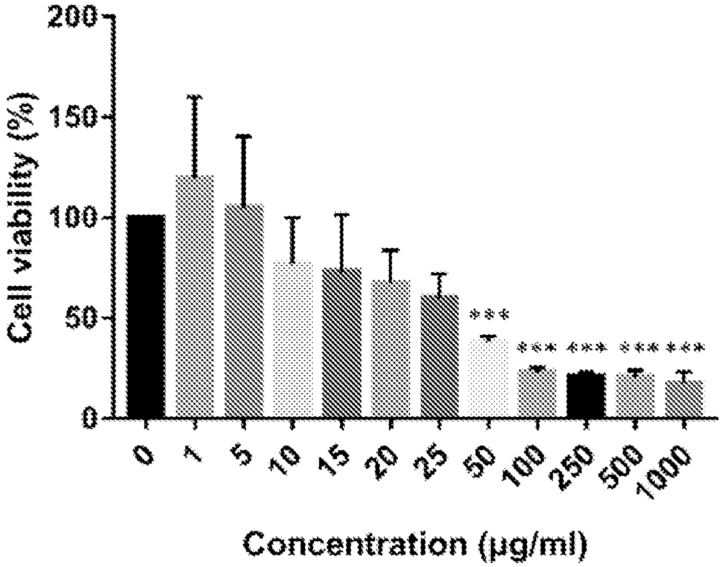
FIG. 2C shows the effects of AR100-DS1 on cell viability, wherein HuS-E/2 cells were treated with 0-1000 μg/ml AR100-DS1 for 48 h, then the MTT assay was performed to detect cell viability (*, P<0.05; , P<0.01; *, P<0.001).
Figure 2D:
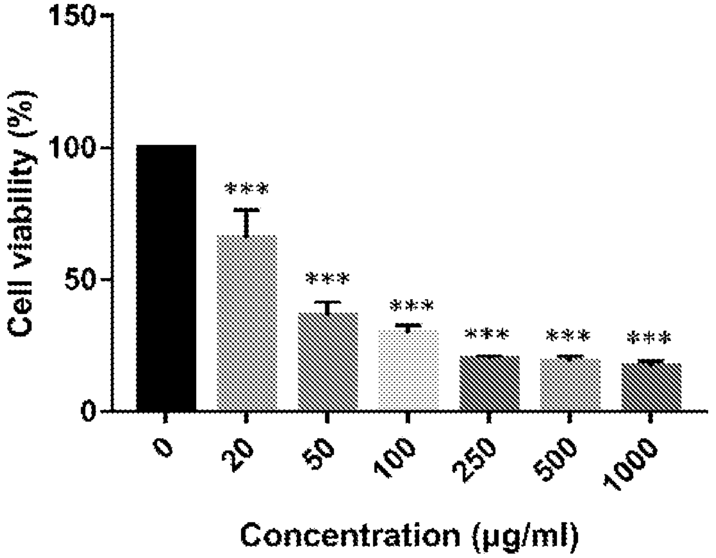
FIG. 2D shows the effects of AR100-DS1 on HepG2.2.15 cells viability (*, P<0.05; , P<0.01; *, P<0.001).

In this study, HepG2.2.15 cells which was stably expressed HBV genome were used to detect the effect of AR100-DS1 on HBV morphogenesis. These results showed that AR100-DS1 significantly inhibited HBV replication, the assembly or release of viral particles. A marked dose-dependent reduction in cell viability was shown in FIGS. 2C (HuS-E/2) and 2D (HepG2.2.15).

Given the results showing the inhibition effects of AR100-DS1 on the secretion of HBsAg and the cell viability of HuS-E/2 cells and HepG2.2.15 cells, it can be concluded that AR100-DS1 can inhibit HBV infection and is potent to develop a drug for treating and/or preventing a virus infection, particularly HBV.

The above description merely relates to preferred embodiments in the present invention, and it should be pointed out that for a person of ordinary skill in the art, some improvements and modifications can also be made under the premise of not departing from the principle of the present invention, and these improvements and modifications should also be considered to be within the scope of protection of the present invention.

2.3 Effect of AR100-DS1 on Inhibition of SARS-COV-2 Infection

Figure 3A:
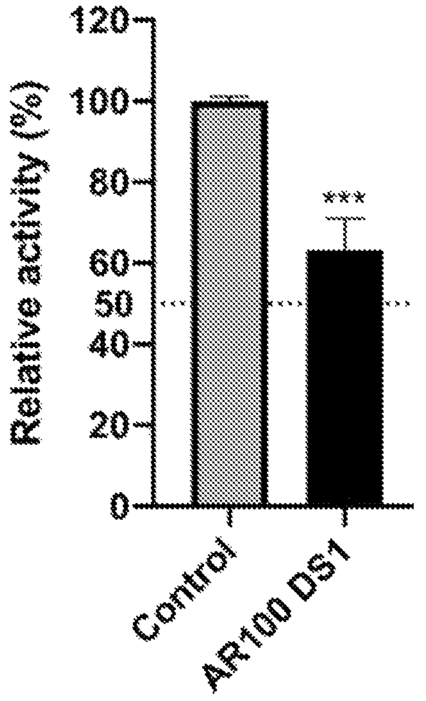
FIG. 3A shows the inhibitory profiles of AR100-DS1 at the concentration of 20 μM. *, P<0.05; , P<0.01; *, P<0.001.
Figure 3B:
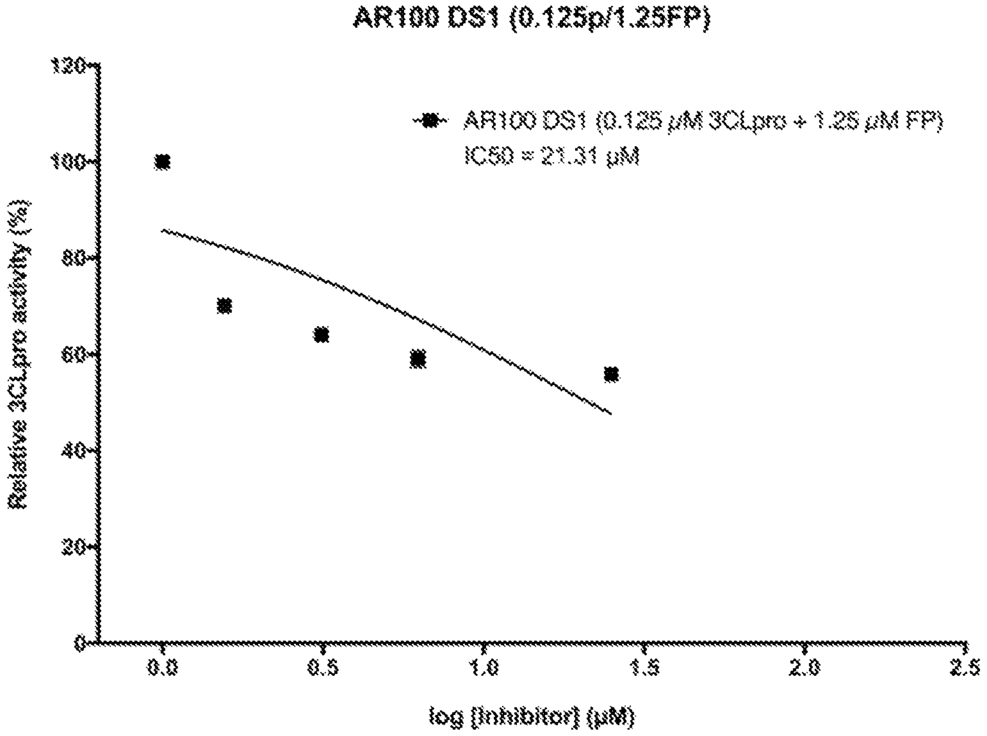
FIG. 3B shows the relative 3CLpro activity (%) of AR100-DS1 (0.125 p/1.25 FP), and IC50=21.31 μM.

The inhibitory profiles of AR100-DS1 at the concentration of 20 μM was determined and the results were given in FIG. 3A. As shown in FIG. 3A, the half maximal inhibitory concentration (IC) toward SARS-COV-2 3CLpro was characterized by treating the compounds at the indicated concentrations ranging from 0 μM to 200 μM. The IC50 values of AR100-DS1 were given in FIG. 3B. AR100-DS1 had an IC50 value of 21.31 μM in the presence of 0.125 μM SARS-COV-2 3CLpro and 1.25 μM IQF peptide substrate.

To confirm the antiviral activities of AR100-DS1 to a coronavirus, the antiviral activities of AR100-DS1 and AR100-DS1+RDV ( ) against SARS-COV-2 in Vero E6 cells was evaluated by the plaque reduction assay. To confirm the antiviral activities of AR100-DS1+RDV on SARS-COV-2, the AR100-DS1 and RDV were prepared individually, then added together during the experiment. AR100-DS1 and RDV were prepared individually and added together, and the results were shown in Table 1 below. The unexpected improved effect of the combination of RDV and AR100-DS1 at 1 μM was observed among the effects of the 10 μM, 5 μM, and 1 μM of AR100-DS1 in combination with 1 μM of RDV. As compared with the effect of the RDV only, the plaque inhibition percentage after the treatment of 1 μM of AR100-DS1 combined with RDV increased from 82% to 98%.

TABLE 1

| | Plaque number per well | | Inhibition (%) to virus | | Inhibition (%) to DMSO | |
|---|---|---|---|---|---|---|
| | mean | SD | mean | SD | mean | SD |
| Control | 174 | 14.6 | | | | |
| DMSO | 159 | 19.1 | 9% | 11% | | |
| 10 μM DS1 + 1 μM RDV | 26 | 0.9 | 85% | 1% | 84% | 1% |
| 5 μM DS1 + 1 μM RDV* | 31 | 6.3 | 82% | 4% | 80% | 4% |
| 1 μM DS1 + 1 μM RDV* | 29 | 0.3 | 84% | 0% | 82% | 0% |
| 1 μM DS1 + RDV* | 4 | 0.7 | 98% | 0% | 97% | 0% |
| 1 μM RDV* | 32 | 1 | 82% | 1% | 80% | 1% |

While preferred embodiments of the present invention have been shown and described herein, it will be obvious to those skilled in the art that such embodiments are provided by way of example only and can be implemented in combinations. Numerous variations, changes, and substitutions will now occur to those skilled in the art without departing from the invention. It should be understood that various alternatives to the embodiments of the invention may be employed in practicing the disclosure. It is intended that the following claims define the scope of the invention and the methods and structures within the scope of these claims and their equivalents be covered thereby.

REFERENCES

1. Ganem, D. and A. M. Prince, Hepatitis B virus infection-natural history and clinical consequences. N Engl J Med, 2004. 350(11): p. 1118-29.
2. Beasley, R. P. Hepatitis B virus. The major etiology of hepatocellular carcinoma. Cancer, 1988.61(10): p. 1942-56.
3. Zoulim, F. and S. Locarnini, Hepatitis B virus resistance to nucleos(D)ide analogues. Gastroenterology. 2009. 137 (5): p. 1593-608 el-2.
4. Chen, W. N. and C. J. Oon, Human hepatitis B virus mutants: significance of molecular changes. FEBS Lett, 1999. 453(3): p. 237-42.
5. Yan, H., et al., Sodium taurocholate cotransporting polypeptide is a functional receptor for buman hepatitis B and D virus. Elife. 1: p. e00049.
6. Watashi, K., et al., NTCP and beyond; opening the door to unveil hepatitis B virus entry. Int J Mol Sci. 15(2): p. 2892-905.
7. Gripon, P., et al., Infection of a human hepatoma cell line by hepatitis B virus. Proc Natl Acad Sci USA, 2002. 99(24): p. 15655-60.
8. Urban, S. and P. Gripon, Inhibition of duck hepatitis B virus infection by a myristoylated pre-S peptide of the large viral surface protein. J Virol, 2002. 76(4): p. 1986-90.
9. Abou-Jaoude, G., et al., Myristoylation signal transfer from the large to the middle or the small HBV envelope protein leads to a loss of HDV particles infectivity. Virology, 2007. 365(1): p. 204-9.
10. Chai, N., et al., Assembly of hepatitis B virus envelope proteins onto a lentivirus pseudotype that infects primary human hepatocytes. J Virol, 2007. 81(20): p. 10897-904.
11. Gudima, S., et al., Primary human hepatocytes are susceptible to infection by hepatitis delta virus assembled with envelope proteins of woodchuck hepatitis virus. J Virol, 2008. 82(15): p. 7276-83.

12. Corey L, Spear P G. Infections with herpes simplex viruses. *New Engl J Med* 1986; 314: 686-691.
13. Ahmed R, Morrison L A, Knipe D M. Persistence of viruses, In: Fields B N, Knipe D M, Howley P M, eds. *Field's Virology*. Philadelphia: Lippincott-Raven Publishers, 1996: 219-250.
14. Contreras A, Slots J. Herpesviruses in human periodontal disease. *J Periodontal Res* 2000: 35: 3-16.
15. Parra B. Slots J. Detection of human viruses in periodontal pockets using polymerase chain reaction. *Oral Microbiol Immunol* 1996; 11:289-293.
16. Ling L-J, Ho C-C, Wu C-Y, Chen Y-T, Hung S-L. Association between human herpesviruses and the severity of periodontitis. *J Periodontol* 2004; 75: 1479-1485.
17. Contreras A, Slots J. Mammalian viruses in human periodontitis. *Oral Microbiol Immunol* 1996; 11: 381-386.
18. Park N H. Virology, In: Nisengard R J, Newman M G, eds. *Oral Microbiology Immunology*. Philadelphia: W. B. Saunders Company, 1994: 248-285.
19. Yura Y, Iga H, Kondo Y, et al. Herpes simplex virus type 1 and type 2 infection in human oral mucosa in culture. *J Oral Pathol Med* 1991; 20: 68-73.
20. Rones Y, Hochman N, Ehrlich J, Zakay-Rones Z. Sensitivity of oral tissues to herpes simplex virus—in vitro. *J Periodontol* 1983: 54: 91-95.
21. Hung S-L, Wang Y-H, Chen H-W, Lee P-L, Chen Y-T. Analysis of herpes simplex virus entering into cells of oral origin. *Virus Res* 2002; 86: 59-69.
22. Furman P A, St Clair M H, Spector T. Acyclovir triphosphate is a suicide inactivator of the herpes simplex virus DNA polymerase. *J Biol Chem* 1984; 259: 9575-9579.
23. Morfin F, Thouvenot D. Herpes simplex virus resistance to antiviral drugs. *J Clin Virol* 2003; 26: 29-37.
24. Field H J. Herpes simplex virus antiviral drug resistance—current trends and future prospects. *J ClinVirol* 2001; 21: 261-269.
25. Chen, C.-N., Lin, C. P. C., Huang, K.-K., Chen, W.-C., Hsieh, H.-P., Liang, P.-H., & Hsu, J. T. A. (2005). Inhibition of SARS-COV 3C-like Protease Activity by Theaflavin-3,3'-digallate (TF3). Evidence-based complementary and alternative medicine: eCAM, 2(2), 209-215. doi: 10.1093/ecam/neh081
26. Hegyi, A., Friebe, A., Gorbalenya, A. E., & Ziebuhr, J. (2002). Mutational analysis of the active centre of coronavirus 3C-like proteases. Journal of General Virology, 83(3), 581-593.
27. Needle, D., Lountos, G. T., & Waugh, D. S. (2015). Structures of the Middle East respiratory syndrome coronavirus 3C-like protease reveal insights into substrate specificity. Acta Crystallographica Section D: Biological Crystallography, 71(5), 1102-1111.
28. Herold, J., Gorbalenya, A. E., Thiel, V., Schelle, B., & Siddell, S. G. (1998). Proteolytic processing at the amino terminus of human coronavirus 229E gene 1-encoded polyproteins: identification of a papain-like proteinase and its substrate. Journal of Virology, 72(2), 910-918.
29. Jo, S. Kim, S. Shin, D. H., & Kim, M.-S. (2020). Inhibition of SARS-COV 3CL protease by flavonoids. Journal of enzyme inhibition and medicinal chemistry, 35(1), 145-151.
30. Coronavirus disease 2019 (SARS-COV-2) Situation Report—28. (2020). Retrieved from https://www.who.int/emergencies/diseases/novel-coronavirus-2019/situation-reports;
31. Li, G., & De Clercq, E. (2020). Therapeutic options for the 2019 novel coronavirus (SARS-CoV-2). In: Nature Publishing Group.
32. De Clercq, E., & Li, G. (2016). Approved antiviral drugs over the past 50 years. Clinical microbiology reviews, 29(3). 695-747.
33, Liu, W., Morse, J. S., Lalonde, T., & Xu, S. (2020). Learning from the Past: Possible Urgent Prevention and Treatment Options for Severe Acute Respiratory Infections Caused by 2019-nCoV. ChemBioChem.
34. Zumla, A., Chan, J. F. Azbar, E. L. Hui, D. S., & Yuen, K.-Y. (2016). Coronaviruses—drug discovery and therapeutic options. Nature reviews Drug discovery, 15(5), 327.
35. Wang, M., Cao, R., Zhang, L., Yang, X., Liu, J., Xu, M., . . . Xiao. G. (2020). Remdesivir and chloroquine effectively inhibit the recently emerged novel coronavirus (SARS-COV-2) in vitro. Cell Research, 1-3.
36. Feng, J. Y. (2018). Addressing the selectivity and toxicity of antiviral nucleosides. Antiviral Chemistry and Chemotherapy, 26, 2040206618758524. doi:10.1177/2040206618758524
37. Jean, F., Basak, A., DiMaio, J., Seidah, N., & Lazure, C. (1995). An internally quenched fluorogenic substrate of prohormone convertase 1 and furin leads to a potent prohormone convertase inhibitor. Biochemical Journal, 307(3), 689-695.
38. Huang, H. C, et al., Entry of hepatitis B virus into immortalized human primary hepatocytes by clathrin-dependent endocytosis. J Virol. 86(17): p. 9443-53.
39. Lin S C, Liu C J, Chiu C P, Chang S M, Lu S Y, Chen Y J. Establishment of OC3 oral carcinoma cell line and identification of NF-kappa B activation responses to areca nut extract. *J Oral Pathol Med* 2004: 33: 79-86.

What is claimed is:

1. A method for treating an infection of hepatitis B virus (HBV), comprising administering to a subject in need thereof a compound which is

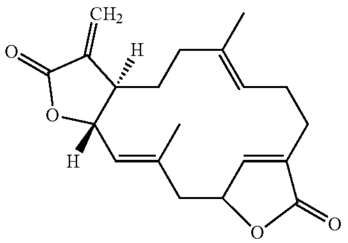

(ovatodiolide)

or a pharmaceutically acceptable salt thereof.

* * * * *